(12) United States Patent
Ramalho et al.

(10) Patent No.: US 7,494,668 B2
(45) Date of Patent: Feb. 24, 2009

(54) FAST WATER-DISPERSIBLE DOMPERIDONE TABLETS

(75) Inventors: Maria Julia Caeiro Ramalho, Sacavem (PT); Micul Hasmuklal Mulchande, Santo Antonio dos Cavaleiros (PT)

(73) Assignee: Laboratorio Medinfar-Produtos Farmaceuticos, S.A., Venda Nova (PT)

( * ) Notice: Subject to any disclaimer, the term of this patent is extended or adjusted under 35 U.S.C. 154(b) by 417 days.

(21) Appl. No.: 11/058,234

(22) Filed: Feb. 16, 2005

(65) Prior Publication Data

US 2006/0051414 A1    Mar. 9, 2006

(30) Foreign Application Priority Data

Sep. 9, 2004    (EP) ................................. 04398007

(51) Int. Cl.
    *A61K 9/20*      (2006.01)
    *D04H 1/00*      (2006.01)

(52) U.S. Cl. ........................ 424/464; 424/465
(58) Field of Classification Search ................. 424/464, 424/465, 466; 514/424
See application file for complete search history.

(56) References Cited

U.S. PATENT DOCUMENTS

2002/0071864 A1 *   6/2002   Kim et al. .................... 424/464
2003/0185886 A1 *   10/2003   Lee et al. ..................... 424/465

* cited by examiner

*Primary Examiner*—Michael G Hartley
*Assistant Examiner*—Jagadishwar R Samala
(74) *Attorney, Agent, or Firm*—Sughrue Mion, PLLC

(57) ABSTRACT

The present invention relates to fast water-dispersible tablets containing domperidone for oral administration. The formulations comprise domperidone or pharmaceutically acceptable salts thereof, about 60-80% of a "auxiliary" granulate (w/w), and about 10-30% of microcrystalline cellulose (w/w), expressed in relation to the total weight of the tablets, a sweetener, a flavouring agent and a lubricant. The "auxiliary" granulate is obtained by wet granulation of D-mannitol and maize starch gum in a high shear granulator, it facilitates the flowability and the compressibility of the mixture and, because of its high solubility in water, contributes to the fast dispersion of the tablet. The formulations have an enhanced structural integrity, for instance having a friability lower than 1.0% and hardness values between 3 and 6 Kp, and are able to disperse in water within 3 minutes, preferably within 2 minutes and most preferably within 1 minute, to provide a dispersion that passes through a 710 μm diameter mesh size sieve and presents a pleasant taste and the absence of perceptible granules in the mouth. This invention also refers to the process for the preparation of said pharmaceutical preparations.

16 Claims, 2 Drawing Sheets

(a)

(b)

FAST WATER-DISPERSIBLE DOMPERIDONE TABLETS

FIELD OF THE INVENTION

The present invention relates to fast water-dispersible tablets containing domperidone or pharmaceutically acceptable salts thereof for oral administration. The formulations comprise domperidone, about 60-80% of a "auxiliary" granulate (w/w), and about 10-30% of microcrystalline cellulose (w/w), expressed in relation to the final weight of the tablets, a sweetener, a flavouring agent and a lubricant.

Most water-dispersible tablets present high percentages of disintegrating agents that tend to weaken the tablet's structure leading to high friability and low hardness values. There are descriptions of other water-dispersible tablets which contain microparticles that swell in contact with the aqueous medium; in these tablets, these microparticles are perceived as individual grains in the mouth in an unpleasant manner. In general, water-dispersible tablets are also very porous and very sensitive to humidity. To prevent all the disadvantages described above, the present invention proposes a formulation with lower percentages of disintegrating agents than the known formulations and that uses an "auxiliary" granulate characterised by its high solubility in water, to improve the disintegration time of the tablets and the respective dissolution of the active ingredient. The use of the "auxiliary" granulate provides the reduction of the percentage of disintegrating agents which are responsible for the above mentioned problems related to the low hardness and high friability values of the tablets. The "auxiliary" granulate is obtained by wet granulation of D-mannitol with maize starch gum to a final percentage of 3% maize starch and 97% of D-mannitol. Mannitol granules work as an "auxiliary" or as a "facilitator" of the flowability and compressibility of the mixture and contributes to the fast dispersion of the tablet, due to its high solubility in water. The formulations have an enhanced structural integrity, for instance having a friability lower than 1.0%, present hardness values between 3 and 6 Kp, and are able to disperse in water within 3 minutes, preferably within 2 minutes and most preferably within 1 minute, to provide a dispersion that passes through a 710 μm diameter mesh size sieve and presents a pleasant taste and the absence of perceptible granules in the mouth.

This invention also refers to the process for the preparation of said pharmaceutical preparations.

BACKGROUND OF THE INVENTION

Domperidone, 5-chloro-1-[1-[3-(2-oxo-2,3-dihydro-1H-benzimidazol-1-yl)propyl]piperidine-4-yl]-1,3-dihydro-2H-benzimidazol-2-one, is a weak base (pKa=7.89) practically insoluble in water and with a lipid to water ratio (log P) of 3.90. It is a potent peripheral dopamine$_2$ antagonist that exerts its gastrokinetic action by acting on the peripheral dopamine$_2$ receptors in the stomach and is a unique compound with both gastrokinetic and antiemetic activity. Unlike metoclopramide, another dopamine-receptor antagonist, domperidone does not readily cross the blood-brain barrie, therefore it has rather minimal extrapyramidal side effects. Clinically, domperidone has been shown to be useful in the treatment of various gastric motility disorders, namely chronic and subacute gastritis, to prevent GI symptoms associated with the use of dopamine agonists in Parkinson's disease, in diabetic gastroparesis, in anorexia nervosa and in patients with postvagotomy gastroparesis.

Therapeutically active compounds are frequently administered to patients in the form of a tablet when the drug is intended for oral administration, since tablets are an especially convenient pharmaceutical form for manufacture, storage and general usage. However, problems may arise with the administration of such tablets to patients who have difficulty in swallowing, for example children, elderly people or more seriously ill patients, especially if the tablets are large in size. Suspension dosage forms could solve this problem, but they have other drawbacks: they have to be reconstituted prior to administration and, sometimes, stored under refrigerated conditions to prevent them from deterioration. Suspensions are also inconvenient to carry while travelling and also involve the risk of inaccurate measurement and dosing. Freeze drying processes have been used to prepare fast disintegrating dosage forms. Depending on the manufacturing process, the product obtained is characterised by a highly porous microstructure of the soluble supporting agent in which the active ingredient is homogeneously dispersed. Although this technology originates a product which rapidly disintegrates in water or in the oral cavity, a drawback is represented by the poor physical integrity of its physical structure, which severely limits further manufacturing operations such as forming blister packs. Another significant drawback of the freeze drying technology is the high production cost, due to the long freeze drying cycles and the complexity and specificity of industrial plants, important factors which prejudice the large scale use of this technology for the development of rapid disintegrating tablets.

Another type of water-dispersible tablets includes effervescent formulations which rely on the formation of a gas to quickly break up the tablet, but these also involve expensive manufacturing methods and strict regulations for such manufacture.

There is a need for dosage forms which would have the convenience of administration of the suspensions and all the advantages of the tablets and capsule formulations. A dispersible tablet is one dosage form that meets these needs. They are easy to carry and can be accurately a conveniently reconstituted in water or aqueous medium immediately before its administration to patients, thus avoiding the need to store solutions or dispersions with risk of hydrolysis. The patient should easily drink the obtained dispersion.

Rapidly disintegrating tablets are known from EP 0 211 946 or WO 8604817, which describe a controlled release potassium chloride tablet that comprises potassium chloride crystals having a mesh size of about 30 to about 50 mesh which are coated with ethylcellulose and hydroxypropylcellulose. The tablets disintegrate rapidly in an aqueous environment, however these tablets contain microparticles that when ingested are perceived as individual grains in the mouth in an unpleasant manner.

EP 0 685 231, U.S. Pat. Nos. 4,886,669 and 5,698,226 patents, describes water-dispersible tablets containing lamotrigine and 0.25 to 40% w/w of a pharmaceutically acceptable swellable clay which is present within the granules of a tablet. However, the use of swellable clays cans undesirable retard the disintegration time of the tablet.

EP 1 058 538 refers to fast disintegrating tablets comprising a drug in multiparticulate form, one or more water insoluble inorganic excipients, one or more disintegrating agents and, optionally, one or more substantially water soluble excipients, the amount of said ingredients being such as to provide a disintegration time for the tablet in the order of 75 seconds or less, typically 30 seconds or less. The water-soluble components are in the range of 0-25% of the total formulation by weight, most preferably about 4-16% by weight. The substantially water insoluble inorganic filler is dibasic calcium phosphate, hydrated or anhydrous.

EP 1 156 786 concerns to fast disintegrating tablets such as those designed to dissolve in the mouth in contact with saliva in less than 30 seconds forming a easy-to-swallow suspension and based on an active substance in the form of coated microcrystals or microgranules and a mixture of carriers comprising at least a disintegrating agent, a soluble agent and a lubricant agent.

EP 1 331 001 patent describes new galenic dispersible and soluble paracetamol formulations comprising a mixture of paracetamol and citric acid in a proportion of 85:15 to 90:10 w/w among other pharmaceutically acceptable components, in an exsiccation state corresponding to a water percentage of less than 0.6% and it is in the form of powder, granulate or tablet.

EP19990941105 application refers to a dosage form that rapidly disintegrates in the mouth and forms viscous slurry of either microcapsules or a powder.

EP19970927372 application refers to intraorally rapidly disintegrable tablet comprising a sugar alcohol or saccharide having an average particle diameter of not more than 30 μm, an active ingredient and a disintegrating agent.

EP19990954046 application concerns an improved multiparticulate tablet disintegrating in the mouth in contact with saliva in less than 40 seconds, characterised by particles of coated active principle, said particles having intrinsic compression properties, and by a mixture of carriers being the proportion of carriers mixture relative to coated active principle particles 0.4 to 0.6 parts by weight.

EP20000113571 application discloses a flash-melt pharmaceutical dosage form comprising a medicament and a combination of four excipients consisting of a superdisintegrant, a dispersing agent, a distributing agent and a binder. The four excipients may be dry granulated with the active ingredient and suitable conventional ingredients.

EP20010904162 application refers to a water-dispersible formulation of paroxetine for immediate oral administration that comprises a dry blend of paroxetine, a water-soluble dispersing agent selected from polyvinyl pyrrolidone, calcium carbonate and sodium starch glycolate, and a taste-masking agent, selected from potassium form polyacrylic acid ion exchange resins, β-cyclodextrin, lecithin and methacrylic acid copolymers, presented as a dispersible powder or moulded into a tablet.

EP20020727563 application relates to fast disintegrating tablets obtained by direct compression comprising meloxicam or a pharmaceutical acceptable salt thereof, containing 20-50% (w/w) of starch and free of cellulose.

EP20030764046 application relates to a process for the preparation of a dispersible tablet dosage form comprising β-lactam antibiotics for oral administration and a disintegrating agent being used both intragranularly and extragranularly.

EP20030706747 application relates to fast disintegrating tablets comprising an active ingredient and one or more disintegrating agents characterised in that the tablets comprise agglomerates having agglomerated particles of at least 50 βm, said agglomerates comprising at least 10% by weight of a superdisintegrating agent selected from croscarmellose cellulose, crospovidone and sodium starch glycolate and being free of active ingredient.

EP20030769384 application relates to dispersible tablets comprising deferacirox or pharmaceutically acceptable salts thereof in an amount of from 5 to 40% in weight by weight of the total tablet and comprising at least one filler in a total amount of about 35 to 55%, at least one disintegrating agent in a total amount of about 10 to 35%, at least one binder in a total amount of 1.5 to 5%, at least one surfactant in a total amount of about 0.2 to 1%, at least one glidant in a total amount of about 0.1 to 0.5% and at least one lubricant in a total amount of less than about 0.4% in weight, all of them expressed in relation of the total weight of the tablet.

EP20030784317 application relates to dispersible tablets of cephalexin comprising granulation of cephalexin with disintegrating agent and colloidal silicon dioxide and binder solution to form granules, drying and mixture of the granules with disintegrating agents, fillers, lubricants and, optionally, other excipients.

WO2004/000281 application relates to rapidly disintegrating tablets intended to be used as orodispersible tablets or dispersible tablets. They are ingested either by dispersing directly in the mouth or in water and contain silicified microcrystalline cellulose.

There are several formulations for good-disintegrating tablets, but said tablets have several disadvantages. Normally those tablets have high percentages of disintegrating agents and are very porous, thus very sensitive to humidity. Moreover, the presence of such ingredients tends to weaken the tablet's structure, leading to high friability and low hardness values. The aim of the present invention is to avoid the above-mentioned inconvenient and provide a fast water-dispersible tablet comprising domperidone to provide a dispersion which will pass through a 710 μm diameter mesh size sieve, which is capable of dispersing in water within 3 minutes, preferably within 2 minutes and most preferably 1 minute, having an enhanced structural integrity, for instance having a friability lower than 1.0%, with a pleasant taste and the absence of perceptible granules in the mouth. The present invention also discloses the process to obtain the above-mentioned formulations.

None of the prior art describes fast water-dispersible tablets containing domperidone.

SUMMARY OF THE INVENTION

The present invention relates to fast water-dispersible tablets containing domperidone for oral administration. The formulations comprise domperidone or pharmaceutically acceptable salts thereof, about 60-80% of mannitol granules (w/w), about 10-30% of microcrystalline cellulose (w/w), expressed in relation to the total weight of the tablets, a sweetener and flavouring agent and a lubricant to provide a dispersion that will pass through a 710 μm mesh sieve. The said formulations are able to disperse in water within 3 minutes, preferably within 2 minutes and most preferably 1 minute, having an enhanced structural integrity, for instance having a friability lower than 1.0% and hardness values between 3 and 6 Kp, and present a pleasant taste and the absence of perceptible granules in the mouth.

The component elements of the dosage form are:
(1) The active ingredient, domperidone
(2) "Auxiliary" granulate
(3) Disintegrating agents
(4) Sweetening agents
(5) Flavouring agents
(6) Lubricants The active ingredient, domperidone or pharmaceutically acceptable salts thereof, are pre-mixed or associated with a half part of the microcrystalline cellulose, blended and calibrated through a 0.7 mm diameter mesh size sieve and this pre-mixture blended with the "auxiliary" granulate and the remaining microcrystalline cellulose and blended, added with the other excipients, namely sweetening and flavouring agents and blended, finally added with the lubricant and, at last, blended for a short time.

Mannitol granules are prepared by high shear granulation with 13% of maize starch gum and, after drying to 3.0% moisture, contain about 3% of maize starch and 97% of D-mannitol (w/w). After drying, mannitol granules are calibrated through a 1 mm diameter mesh size sieve.

The present invention also makes available the mannitol granules, their preparation and their use in fast water dispersible tablets.

The present invention also discloses the process to obtain the mentioned formulations.

DETAILED DESCRIPTION OF THE INVENTION

Figure 1:
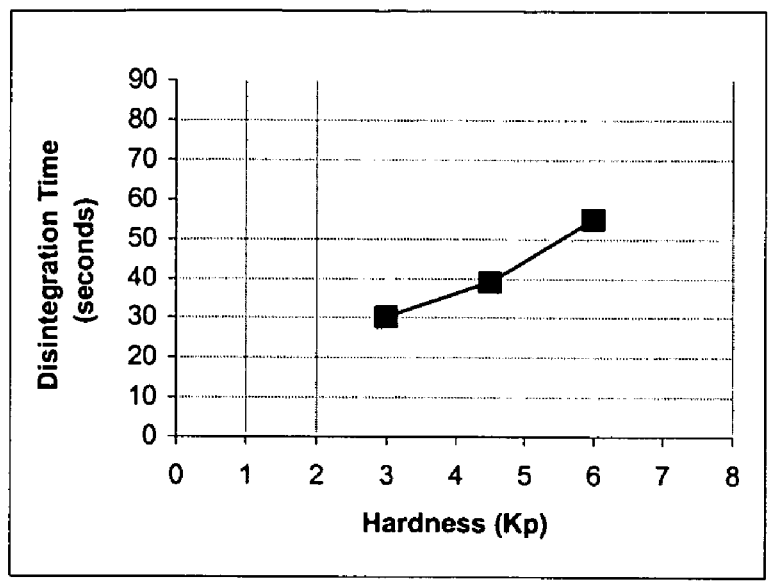
FIG. 1 presents the effect of hardness on the disintegration time (a) and on the friability (b) of the water-dispersible domperidone tablets of the present invention. The results show that with hardness values between 3 and 6 Kp, disintegration times are between 30 and 55 seconds (a) and the respective friabilities are maintained between 0.6 and 0.3% (b). The results suggest that with hardness values higher than 6 Kp, disintegration times should be higher than 1 minute, which is not intended.
Figure 1:
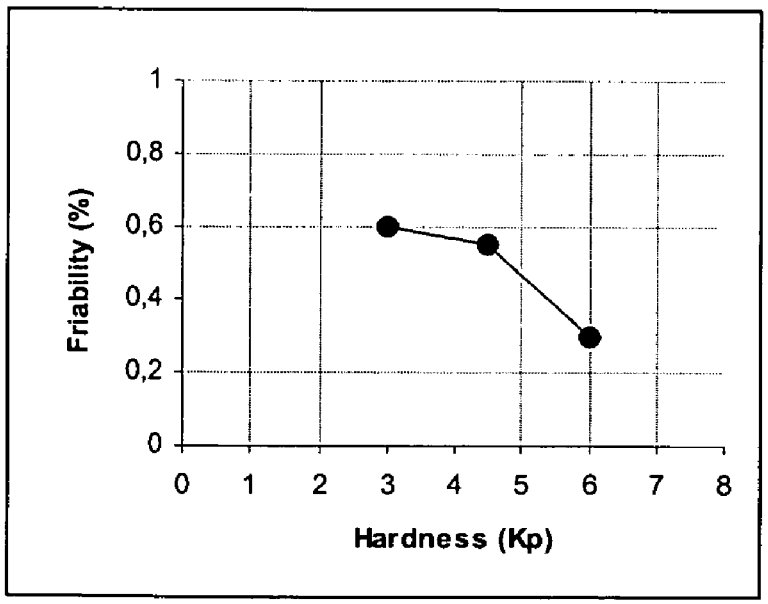

By "dispersible tablet" is meant a tablet which disperses in aqueous phase, e.g. in water before administration. A water-dispersible tablet, according to the British Pharmacopoeia and European Pharmacopoeia, should meet the requirements of the test for dispersible tablets as regards dispersion time (<3 minutes) and dispersion quality (i.e. to pass through a 710 µm sieve). The present invention discloses a fast water-dispersible tablet containing domperidone which is able to disperse in water within 3 minutes, preferably within 2 minutes and most preferably within 1 minute, having an enhanced structural integrity, for instance having a friability lower than 1.0% and hardness values between 3 and 6 Kp, to provide a dispersion which will pass through a 710 µm sieve, with pleasant taste and the absence of perceptible granules in the mouth.

The present invention also discloses the process to obtain the mentioned formulations.

The component elements of the dosage form are:
(1) Domperidone
(2) "Auxiliary" granulate
(3) Disintegrating agents
(4) Sweetening agents
(5) Flavouring agents
(6) Lubricants The active ingredient, domperidone, is a white powder practically insoluble in water. It should be used as it is, or in the form of a pharmaceutically acceptable salt, for instance maleate, which is soluble in water. In the present invention the active is not micronised.

Mannitol is a polyol molecule very soluble in water and with a very pleasant taste. Most water-dispersible tablets reported use large amounts of disintegrating agents in order to assure the easy disintegration of the tablet in water. The main disadvantage of the use of very high percentages of disintegrating agents is the low hardness, the high porosity and the high sensitivity to moisture of the tablets. In the present invention, in order to obtain a good dispersibility of the domperidone tablets we use a "auxiliary" granulate comprising D-mannitol characterised by its very high water-solubility. To improve the flowability and the compressibility of the mixture in order to obtain tablets with good properties, we granulated mannitol with maize starch gum. Maize starch gum was prepared by heating maize starch dispersion prepared at 13% (w/w) with purified water. Mannitol granules are prepared in order to contain 3% of maize starch and 97% of mannitol. After drying at 45±5° C. to moisture value <3.0% (Karl-Fischer method), granules were calibrated through a 1.0 mm diameter mesh size sieve. These mannitol granules work as a "auxiliary" granulate that facilitates the flowability and compressibility of the final mixture and, at the same time, contribute to the fast water dispersion of the formulation due to its very high solubility in water. The mannitol granules obtained can be mixed with the active ingredient and with the remaining excipients and compressed.

Several disintegrating agents like microcrystalline cellulose (i.e. Avicel PH101), pregelatinized maize starch (i.e. Starch 1500), sodium starch glycolate (Explotab) and calcium carboxymethylcellulose are tested in the present invention. In general, we use amounts of disintegrating agents lower than those used by others. Examples show different formulations with different amounts of disintegrants used alone or mixed together.

Sweetening agents are used to improve the taste of the dispersion. Sweeteners used in the present invention may be artificial sweetening agents such as, for example, aspartame, sodium saccharin, acesulfame potassium, or also natural sugars, or other pharmacologically acceptable sweeteners known from the state of the art. Artificial sweeteners are preferred in the present invention because of the interest of the formulation to be administered to diabetics.

Flavouring agents are used to mask the taste of the active substance in the formulation. In the present invention flavouring agents may preferably be selected among conventional flavours, such as natural flavouring agents, nature-identical flavouring agents, and artificial flavouring agents of different tastes.

Lubricants are preferably selected from the group of hydrophobic lubricants such as the hydrogenated fatty oils, magnesium stearate and stearic acid. The preferred lubricant was calcium stearate.

The present invention further provides a process for the preparation of the fast water-dispersible domperidone tablets as defined in the first aspect of the invention, said process comprising the preparation of the mannitol granules, the pre-mixture or association of a half part of microcrystalline cellulose with domperidone and sieving and blending of this pre-mixture, addition of mannitol granules to this pre-mixture and to the remaining part of microcrystalline cellulose and blending, and addition of the other excipients, namely sweetening and flavouring agents, subsequent blending and, at last, addition of the lubricant and blending of the final mixture.

Preferably, said process comprises the following steps:
a) Preparation of the maize starch gum by heating.
b) Preparation of the "auxiliary" granulate by wet granulation of the D-mannitol with the maize starch gum through high shear granulation.
c) Drying of the granulate in fluid bed dryer or horizontal static oven to moisture <3.0%, evaluated by the Karl-Fischer method.
d) Calibration of the granulate through 1.0 mm diameter mesh size sieve.
e) Pre-mixture of domperidone and a half part of disintegrating agent (i.e. microcrystalline cellulose) and calibration through 0.7 mm diameter mesh size sieve.
f) Addition of the pre-mixture with the mannitol granules and the remaining disintegrating agent and blending.
g) Addition of the other excipients such as sweetening and flavouring agents, and blending.
h) Final homogenation of the mixture with the lubricant for a short period of time.

Preferably, the dispersion time of the tablets according to the invention is less than 3 minutes, more preferably less than 2 minutes and most preferably less than 1 minute. The water-dispersible domeperidone tablets meet the requirements of the test for dispersible tablets as regards dispersion time (<3 minutes) and dispersion quality (i.e. to pass through a 710 um sieve) according to the British Pharmacopoeia and European Pharmacopoeia, and have an enhanced structural integrity, for instance a friability lower than 1.0% and hardness values between 3 and 6 Kp, with a pleasant taste and the absence of perceptible granules in the mouth.

The present invention also provides:
a) The preparation of the "auxiliary" granulate of D-Mannitol and maize starch;
b) Use of the mannitol granules as defined above in the preparation of fast water dispersible tablets of domperidone;
c) Fast water-dispersible tablets as defined herein comprising domperidone together with mannitol granules, microcrystalline cellulose, a sweetener, a flavouring agent and a lubricant;
d) A method for the preparation of the fast water-dispersible domperidone tablets which comprises the steps of preparation of the mannitol granules and the preparation of the mixture to be compressed.

The tablets of the present invention may replace the existing paediatric suspension formulations comprising domperidone.

The present invention is illustrated by the Examples 7 to 10, but in no way limited by them. Examples 1 to 6 represent formulations that do not meet the requirements, namely in what concerns friability, disintegration time or both.

EXAMPLES

Examples 1, 2, 3 and 4 are assays that we performed in order to obtain, by direct compression, the fast water-dispersible domperidone tablets with the intended characteristics. In these 4 examples, the tablets were prepared according to the following general method:
a) The dry components were calibrated through convenient mesh size sieves.
b) A dry mixture of all components was made, except sweetener, flavouring agent and lubricant, and blended for 30 minutes.
c) Sweetening and flavouring agents were added and blended for 10 minutes.
d) Lubricant was then added and the final mixture blended for only 3 minutes.

The compositions of the tablets obtained by direct compression are the following:

| Composition | Example 1 per tablet (mg) | % | Example 2 per tablet (mg) | % | Example 3 per tablet (mg) | % | Example 4 per tablet (mg) | % |
| --- | --- | --- | --- | --- | --- | --- | --- | --- |
| Domperidone | 10.00 | 3.8 | 10.00 | 3.8 | 10.00 | 3.8 | 10.00 | 3.8 |
| Microcrystalline Cellulose (Avicel PH101) | 130.00 | 50.0 | 35.00 | 13.5 | 35.00 | 13.5 | 50.00 | 19.2 |
| Lactose (Tablettose 70) | | | 70.00 | 26.9 | 70.00 | 26.9 | 70.00 | 26.9 |
| Mannitol | | | 100.00 | 38.5 | 100.00 | 38.5 | 100.00 | 38.5 |
| Pregelatinised starch (Starch 1500) | 100.0 | 38.5 | 25.00 | 9.6 | | | | |
| Sodium starch glycolate (Explotab) | 1.80 | 0.7 | 1.80 | 0.7 | 26.80 | 10.3 | 11.80 | 4.5 |
| Colloidal silicon dioxide (Aerosil 200) | 0.75 | 0.3 | 0.75 | 0.3 | 0.75 | 0.3 | 0.75 | 0.3 |
| Saccharin Sodium | 6.15 | 2.4 | 6.15 | 2.4 | 6.15 | 2.4 | 6.15 | 2.4 |
| Flavouring agent | 3.30 | 1.3 | 3.30 | 1.3 | 3.30 | 1.3 | 3.30 | 1.3 |
| Stearic acid | 8.00 | 3.1 | 8.00 | 3.1 | 8.00 | 3.1 | 8.00 | 3.1 |
| TOTAL | 260.00 | 100.0 | 260.00 | 100.0 | 260.00 | 100.0 | 260.00 | 100.0 |
| Disintegrating agents | | 89.2 | | 23.8 | | 23.8 | | 23.7 |
| Hardness | 3-6 Kp | | 3-6 Kp | | 3-6 Kp | | 3-6 Kp | |
| Friability | >1.0% | | <1.0% | | <1.0% | | >1.0% | |
| DisintegrationTime | >3 min | | >3 min | | >3 min | | >2 min | |
| Uniformity of dispersion (710 μm) | In accordance | | In accordance | | In accordance | | In accordance | |

The tablets were prepared for a final weight of 260 mg. The intent was to achieve good hardness and friability values and adequate disintegration times for the water-dispersible domperidone tablets. As it can be observed in the table presented above, although hardness values are relatively high, friability and/or disintegration times are out of specification.

Taking into account the results obtained in Examples 1 to 4, we decided to abandon direct compression of mixtures with great amounts of disintegrating agents and adopt the wet granulation of very soluble excipients in combination with lower amounts of disintegrating agents. The very soluble excipient chosen was D-mannitol and the binder agent the maize starch gum.

The mannitol granules were prepared as follows:

Preparation of the Maize Starch Gum:

For wet granulation, the maize starch gum was prepared with 13% (w/w) of maize starch in purified water. The gum was prepared by heating and stirring the maize starch suspension until the increase of viscosity.

| Components | For 1 Kg Maize starch gum |
|---|---|
| Maize Starch | 130 g |
| Purified water | 870 g |
| Total | 1 000 g |

Preparation of Mannitol Granules:

Mannitol granules should contain 3% of maize starch. For the preparation of 1 Kg of Mannitol granules, composition should be as follows:

| Components | For 1 Kg of Mannitol granules |
|---|---|
| Maize Starch gum | 230.8 g* |
| D-Mannitol | 970 g |
| Total | 1 000 g |

*This corresponds to 30 g of maize starch and 3% (w/w) of the total mannitol granules.

a) Mannitol is placed in a high shear granulator and maize starch gum is added.
b) Granulation is done at high speed until granulation is concluded (i.e. for approximately 2 minutes).
c) The wet granules are dried at 45°±5° C. in a fluid bed drier or in a static horizontal oven till <3% moisture measured by the Karl-Fischer method.
d) The granules are then calibrated through a 1.0 mm opening mesh size sieve and can be used as a raw material in the manufacture of the fast water-dispersible domperidone tablets.

Preparation of the Tablets

The following Examples show formulations prepared with the mannitol granules prepared as described above. Pregelatinized starch, sodium starch glycolate and colloidal silicon dioxide were excluded and mannitol granules included in the formulations.

In Examples 5-10, tablets were prepared according to the following general method:

a) Mannitol granules were prepared as described above.
b) The dry components were calibrated through convenient opening mesh size sieves.
c) A pre-mixture with a half part of microcrystalline cellulose and Domperidone was made and blended, then calibrated through a 0.7 mm diameter mesh size sieve.
d) Addition of the mannitol granules to the previous pre-mixture and the other half part of microcrystalline cellulose and blending for 15 minutes.
e) Addition of the remaining ingredients (sweetener and flavour) and blending for 15 minutes.
f) Lubricant was then added and the final mixture homogenised for only 3 minutes.

| Composition | Example 5 per tablet (mg) | % | Example 6 per tablet (mg) | % | Example 7 per tablet (mg) | % |
|---|---|---|---|---|---|---|
| Domperidone | 10.00 | 3.8 | 10.00 | 3.8 | 10.00 | 3.8 |
| Microcrystalline Cellulose (Avicel PH101) | 50.00 | 19.2 | 50.00 | 19.2 | 50.00 | 19.2 |
| Mannitol granules | 180.00 | 69.2 | 183.65 | 70.6 | 188.65 | 72.6 |
| Carboxymetthylcellulose calcium | 8.95 | 3.5 | 5.00 | 1.9 | | |
| Saccharin sodium | 6.15 | 2.4 | 6.15 | 2.4 | 6.15 | 2.4 |
| Flavouring agent | 3.30 | 1.3 | 3.30 | 1.3 | 3.30 | 1.3 |
| Calcium stearate | 1.60 | 0.6 | 1.90 | 0.7 | 1.90 | 0.7 |
| TOTAL | 260.00 | 100.0 | 260.00 | 100.0 | 260.00 | 100.0 |
| Hardness | 3-6 Kp | | 3-6 Kp | | 3-6 Kp | |
| Friability | >1.0% | | >1.0% | | <1.0% | |
| Disintegration Time | <1 min | | <1 min | | <1 min | |
| Uniformity of dispersion (710 µm) | In accordance | | In accordance | | In accordance | |

Tablets were prepared for a final weight of 260 mg. The intent was to achieve hardness values between 3 and 6 Kp, friability values <1.0% and disintegration times preferably <1 min for water-dispersible domperidone tablets. As can be observed in the table, Examples 5 and 6 present two disintegrating agents, microcrystalline cellulose and carboximethylcellulose calcium; in these Examples, hardness values comply, but friability values are out of specification. In Example 7, carboxymethylcellulose calcium was excluded, the amount of microcrystalline cellulose fixed around 20% (i.e. 19.2%) and the amount of mannitol granules was around 70% (i.e. 72.6%). Example 7 displays good performances for the three parameters specified: hardness, friability and disintegration time for the domperidone fast water-dispersible tablets.

In Examples 8 and 9 we tested a change in the proportions of the disintegrating agent (i.e microcrystalline cellulose) and mannitol granules, in order to study the effect of this change in the behaviour of formulations. Example 8 presents around 10% of microcrystalline cellulose (i.e. 11%) and around 80% of Mannitol granules (i.e. 80.8%). Example 9 presents 30% of microcrystalline cellulose and around 60% of Mannitol granules (i.e. 61.8%). Both Examples present good results for the tested parameters.

|  | Example 8 | | Example 9 | |
| --- | --- | --- | --- | --- |
| Composition | per tablet (mg) | % | per tablet (mg) | % |
| Domperidone | 10.00 | 3.8 | 10.00 | 3.8 |
| Microcrystalline Cellulose (Avicel PH101) | 28.65 | 11.0 | 78.01 | 30.0 |
| Mannitol granules | 210.00 | 80.8 | 160.64 | 61.8 |
| Saccharin sodium | 6.15 | 2.4 | 6.15 | 2.4 |
| Flavouring agent | 3.30 | 1.3 | 3.30 | 1.3 |
| Calcium stearate | 1.90 | 0.7 | 1.90 | 0.7 |
| TOTAL | 260.00 | 100.0 | 260.00 | 100.0 |
| Hardness | 3-6 Kp | | 3-6 Kp | |
| Friability | <1.0% | | <1.0% | |
| Disintegration Time | <1 min | | <1 min | |
| Uniformity of dispersion (710 μm) | In accoprdance | | In accoprdance | |

We observed that with higher amounts of microcrystalline, cellulose friability stays out of specification.

In view of the present results, we have concluded that it is possible to obtain fast water-dispersible domperidone tablets of hardness between 3 and 6 Kp, friability lower than 1% and disintegration time below 1 minute, with formulations containing an amount of microcrystalline cellulose between about 10 and 30% (w/w) and mannitol granules between 60 and 80% (w/w), expressed in relation to the total weight of the formulation.

With the following formulation (very similar to Example 7), we studied the effect of hardness on disintegration time and friability of the fast water-dispersible domperidone tablets:

|  | Example 10 | |
| --- | --- | --- |
| Composition | per tablet (mg) | % |
| Domperidone | 10.00 | 3.8 |
| Microcrystalline Cellulose (Avicel PH101) | 50.85 | 19.6 |
| Mannitol granules | 187.80 | 72.2 |
| Saccharin sodium | 6.15 | 2.4 |
| Flavouring agent | 3.30 | 1.3 |
| Calcium stearate | 1.90 | 0.7 |
| TOTAL | 260.00 | |

We observed that, by increasing the hardness of the tablets, the disintegration time also increased. With tablets with hardness values between 3 and 6 Kp, disintegration times were between 30 and 55 seconds (See FIG. 1(a)). Because of this, the hardness of these tablets should not be higher than 6 Kp, in order not to increase the disintegration times to values higher than 1 minute. On the other hand, we observed that with hardness values between 3 and 6 Kp, friability values were between 0.6 and 0.3% respectively (see FIG. 1(b)). The results suggest that hardness should not be lower than 3 Kp or higher than 6 Kp, in order that tablets can comply with the specified values for friability and disintegration time.

Figure 2:
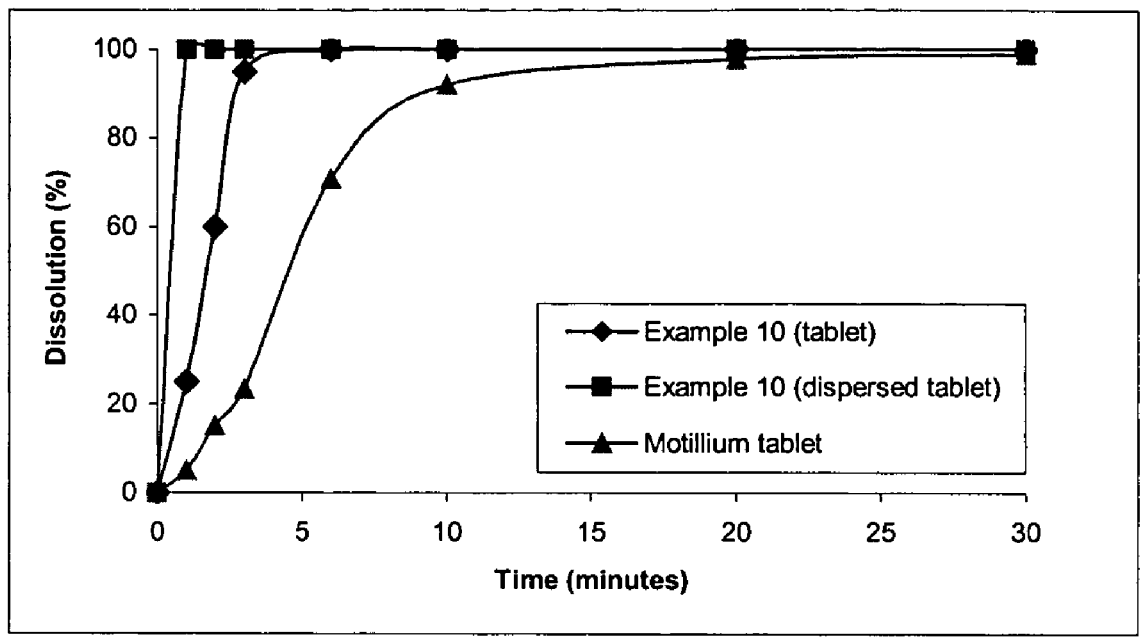
FIG. 2 presents the dissolution profile of Motilium® tablets, of tablets of the present invention prepared according the formulation presented in Example 10, and of a water-dispersion of tablets of the present invention prepared according to the formulation presented in Example 10 and added to the incubation medium. The presented results show that dissolution is more rapid for the water-dispersion prepared with the tablets of the present invention (i.e., 100% dissolution after 1 minute of incubation), after this, for the water-dispersible tablets of the present invention put directly in the incubation medium (i.e. 94.8% of dissolution after 3 minutes of incubation) and, at last, for the Motilium® conventional tablets put directly in the incubation medium (i.e. only 23.2% of dissolution after 3 minutes of incubation). The results suggest that the pharmacological effect produced by the administration of the formulations of the present invention seems to be more rapidly achieved than with conventional tablets.

We also compared the dissolution rate of the fast water-dispersible domperidone formulations of the present invention (i.e. Example 10, batch CND001) with Motilium® tablets obtained on the market (batch 028Q159) (see FIG. 2). Dissolution profiles were performed in a dissolution apparatus with paddles. Tablets were incubated during 30 minutes, in Hydrochloride medium 0.1 M, at pH1.2, stirred at 50 rpm. After the incubation time, the samples were passed through a 0.45 μm filter and analysed by HPLC, with detection at 280 nm. FIG. 2 presents the dissolution profiles obtained for both formulations. The points represent the average value obtained for 6 tablets of each formulation. The data show that after 1, 2 and 3 minutes of incubation the water dispersible domperidone tablets of the present invention released 25.1%, 60.2% and 94.8% of the active ingredient, respectively, whereas Motilium® tablets released, after the same times, only 5.1%, 15.0% and 23.2%. After 6 minutes, the difference between domperidone released by both formulations is still about 30%. Only after 20 minutes of incubation, the amount of domperidone released by both formulations presents similar values. With this experiment, we concluded that the dissolution of domperidone formulations of the present invention is faster than the one of the conventional tablets existing on the market. These results suggest that the pharmacological effect produced by the administration of the formulations of the present invention seems to be more rapidly achieved than with conventional tablets.

Taking into account that the water-dispersible domperidone tablets of the present invention are to be dispersed in water and, after this, ingested by the patient, we performed another experiment to evaluate the dissolution profile of domperidone from the water-dispersed tablet. For this purpose, we dispersed one tablet of the present invention (Example 10 (dispersed tablet)) in 100 ml of water and we added this dispersion to the incubation medium of the dissolution apparatus. The values of domperidone dissolved presented in FIG. 2 have been corrected taking into account the dilution factor.

The results obtained in this experiment show that domperidone is completely dissolved after 1 minute of incubation of the dispersion in the incubation medium. These results suggest that the pharmacological effect of the dispersion obtained after water-dispersion of the tablets of the present invention could be more rapidly produced than by swallowing of the same tablets and much more rapidly than with the Motilium( conventional tablets.

Control of the Finished Product

Tablets were evaluated according to the following methods:

Moisture: Grind 30 water-dispersible domperidone tablets and take a sample of about 260 mg. Evaluate the moisture through the Karl-Fischer method. The value obtained should be <3.0%.

Hardness: Evaluate hardness of 30 dispersible domperidone tablets using a Vanderkam VK200 or Scheuniger 6D apparatus. Values should be between 3 and 6 Kp.

Friability: Evaluate weight loss using a Roche friabilator using 20 water-dispersible tablets of domperidone. Twenty tablets, accurately weighed, were subject to 100 rotations and reweighed afterwards, and the weigh loss due to friability was calculated as a percentage of the initial weight. Results should be <1.0%.

Disintegration Time: Using a disintegration apparatus with bath temperature control and 6 tablets per assay, evaluate the disintegration time in 900 ml purified water, at 15-25° C., as described in the European Pharmacopoeia. Results should be lower than 3 minutes.

Dispersion Quality: In accordance with the European Pharmacopoeia uniformity of dispersion test for dispersible tablets, two tablets were placed in 100 ml of water and allowed to disperse. A smooth dispersion was produced, which passed through a sieve screen with a nominal mesh aperture of 710 (m.

Assay: Weigh and grind 10 dispersible tablets of domperidone. Take about 1.3 g of powder and solubilise it in DMF. Dilute it conveniently in DMF, pass it through 0.45 (m filter and inject it in HPLC with detection at 280 nm. Prepare the external standard of domperidone using the same procedure. Stationary phase is a C18 column (i.e. LiChrospher 100 RP-18 (5 um)) and mobile phase methanol:Ammonium acetate at 0.5% (60:40). The flux used is 1.5 ml/min. Results should be between 9.5 and 10.5 mg/tablet.

Dissolution assay: Perform the assay with 6 tablets, according to the method described in the European Pharmacopoeia, in a dissolution apparatus using 900 ml of Hydrochloride 0.1N, at 37° C.(0.5° C., stirred at 50 rpm, for 30 minutes. After incubation, the medium is filtrated through a 0.45 (m filter paper and injected in HPLC according to the method described for the assay. Values should be higher than 80%.

Impurities: The method is similar to the one used for assay but the mobile phase is a gradient presented as follows:

| Time | Mixture I (%)* | Methanol (%) |
|------|----------------|--------------|
| 0    | 100            | 0            |
| 30   | 27             | 73           |
| 32   | 0              | 100          |
| 34   | 0              | 100          |
| 36   | 100            | 0            |
| 41   | 100            | 0            |

*Mixture I is: Ammonium acetate 0.5% in methanol (70:30).

The external standard for evaluation of impurities comprises domperidone as well as droperidol.

Stability Tests

To test the stability of the pharmaceutical dosage forms of the present invention, a stability protocol was established with 3 different batches of fast water-dispersible domperidone tablets produced according to the invention (i.e. batches CND 001, CND 002 and CND 003). Tablets were blistered in Polyamide/Aluminium/PVC sealed with Aluminium foil of 25 μm and incubated in accelerated conditions at 40° C.±2° C. of temperature and 75%±5% relative humidity during 6 months, and in normal conditions, at 25° C.±2° C. temperature and with a relative humidity of 60%±5%, for 2 years. Several parameters were periodically determined.

The results obtained are presented as follows:

BATCH CND 001—Stability tests performed with blisters of dispersible domperidone tablets at 40° C.±2° C. temperature and 75%±5% relative humidity.

| Parameter | Specification | $T_o$ | 3 months | 6 months |
|-----------|---------------|-------|----------|----------|
| Description | White round tablets | White round tablets | White round tablets | White round tablets |
| Moisture (%) | <3.0 | 1.7 | 1.4 | 1.8 |
| Assay (%) | 95.0-105.0 | 100.0 | 99.8 | 100.3 |
| Hardness (Kp) | 3.0-6.0 | 4.4 | 4.3 | 3.0 |
| Friability (%) | <1.0 | 0.25 | 0.33 | 0.31 |
| Disintegration time (seconds) | <180 (<3 min) | 37 | 37 | 48 |
| Dispersion Quality | Passes through 710 um | in accordance | in accordance | in accordance |
| Dissolution (%) | ≧80.0 | 100.3 | 97.6 | 97.4 |
| Impurities (%) | Indiv: ≦0.5 | 0.4 | 0.4 | 0.2 |
|  | Total: ≦1.0 | 0.8 | 0.9 | 0.4 |

BATCH CND 002—Stability tests performed with blisters of dispersible domperidone tablets at 40° C.±2° C. temperature and 75%±5% relative humidity.

| Parameter | Specification | $T_o$ | 3 months | 6 months |
|-----------|---------------|-------|----------|----------|
| Description | White round tablets | White round tablets | White round tablets | White round tablets |
| Moisture (%) | <3.0 | 1.6 | 1.6 | 1.7 |
| Assay (%) | 95.0-105.0 | 99.9 | 99.7 | 100.0 |
| Hardness (Kp) | 3.0-6.0 | 4.7 | 3.3 | 3.3 |
| Friability (%) | <1.0 | 0.36 | 0.31 | 0.35 |
| Disintegration time (seconds) | <180 (<3 min) | 35 | 40 | 49 |
| Dispersion Quality | Passes through 710 um | in accordance | in accordance | in accordance |
| Dissolution (%) | ≧80.0 | 99.2 | 97.4 | 97.4 |
| Impurities (%) | Indiv: ≦0.5 | 0.4 | 0.3 | 0.3 |
|  | Total: ≦1.0 | 0.7 | 0.9 | 0.5 |

BATCH CND 003—Stability tests performed with blisters of dispersible domperidone tablets at 40° C.±2° C. temperature and 75%±5% relative humidity.

| Parameter | Specification | T$_o$ | 3 months | 6 months |
|---|---|---|---|---|
| Description | White round tablets | White round tablets | White round tablets | White round tablets |
| Moisture (%) | <3.0 | 1.7 | 1.4 | 1.6 |
| Assay (%) | 95.0-105.0 | 100.0 | 99.7 | 101.0 |
| Hardness (Kp) | 3.0-6.0 | 4.4 | 3.5 | 3.0 |
| Friability (%) | <1.0 | 0.35 | 0.29 | 0.23 |
| Disintegration time (seconds) | <180 (<3 min) | 36 | 40 | 49 |
| Dispersion Quality | Passes through 710 um | in accordance | in accordance | in accordance |
| Dissolution (%) | ≧80.0 | 100.1 | 97.2 | 99.5 |
| Impurities (%) | Indiv: ≦0.5 | 0.4 | 0.3 | 0.3 |
|  | Total: ≦1.0 | 0.6 | 0.9 | 0.4 |

BATCH CND 001—Stability tests performed with blisters of dispersible domperidone tablets at 25° C.±2° C. temperature and 60%±5% relative humidity.

| Parameter | Specification | T$_o$ | 3 months | 6 months | 9 months | 12 months | 18 months | 24 months |
|---|---|---|---|---|---|---|---|---|
| Description | White round tablets | White round tablets | White round tablets | White round tablets | White round tablets | White round tablets | White round tablets | White round tablets |
| Moisture (%) | <3.0 | 1.7 | 1.4 | 1.6 | 1.7 | 1.6 | 1.5 | 1.4 |
| Assay (%) | 95.0-105.0 | 100.0 | 99.9 | 100.0 | 99.6 | 100.0 | 98.5 | 97.9 |
| Hardness (Kp) | 3.0-6.0 | 4.4 | 4.6 | 3.5 | 3.5 | 3.1 | 3.3 | 3.2 |
| Friability (%) | <1.0 | 0.25 | 0.29 | 0.25 | 0.25 | 0.33 | 0.29 | 0.27 |
| Disintegration time (seconds) | <180 (<3 min) | 37 | 40 | 42 | 42 | 41 | 47 | 51 |
| Dispersion Quality | Passes through 710 um | in accordance | in accordance | in accordance | in accordance | in accordance | in accordance | in accordance |
| Dissolution (%) | ≧80.0 | 100.3 | 100.2 | 100.1 | 99.9 | 98.5 | 100.6 | 100.8 |
| Impurities (%) | Indiv: ≦0.5 | 0.4 | 0.5 | 0.3 | 0.3 | 0.3 | 0.3 | 0.4 |
|  | Total: ≦1.0 | 0.8 | 0.9 | 0.6 | 0.6 | 0.4 | 0.4 | 0.7 |

BATCH CND 002—Stability tests performed with blisters of dispersible domperidone tablets at 25° C.±2° C. temperature and 60%±5% relative humidity.

| Parameter | Specification | T$_o$ | 3 months | 6 months | 9 months | 12 months | 18 months | 24 months |
|---|---|---|---|---|---|---|---|---|
| Description | White round tablets | White round tablets | White round tablets | White round tablets | White round tablets | White round tablets | White round tablets | White round tablets |
| Moisture (%) | <3.0 | 1.6 | 1.5 | 1.7 | 1.6 | 1.8 | 1.5 | 1.4 |
| Assay (%) | 95.0-105.0 | 99.9 | 99.9 | 100.2 | 100.1 | 100.0 | 100.4 | 99.8 |
| Hardness (Kp) | 3.0-6.0 | 4.7 | 4.6 | 3.0 | 3.5 | 3.5 | 3.3 | 3.4 |
| Friability (%) | <1.0 | 0.36 | 0.36 | 0.37 | 0.38 | 0.29 | 0.23 | 0.41 |
| Disintegration time (seconds) | <180 (<3 min) | 35 | 37 | 38 | 40 | 48 | 50 | 56 |
| Dispersion Quality | Passes through 710 um | in accordance | in accordance | in accordance | in accordance | in accordance | in accordance | in accordance |
| Dissolution (%) | ≧80.0 | 99.2 | 99.6 | 100.1 | 99.0 | 98.0 | 99.2 | 100.4 |
| Impurities (%) | Indiv: ≦0.5 | 0.4 | 0.3 | 0.3 | 0.3 | 0.3 | 0.3 | 0.4 |
|  | Total: ≦1.0 | 0.7 | 0.8 | 0.5 | 0.4 | 0.4 | 0.5 | 0.7 |

BATCH CND 003—Stability tests performed with blisters of dispersible domperidone tablets at 25° C.±2° C. temperature and 60%±5% relative humidity.

| Parameter | Specification | $T_o$ | 3 months | 6 months | 9 months | 12 months | 18 months | 24 months |
|---|---|---|---|---|---|---|---|---|
| Description | White round tablets | White round tablets | White round tablets | White round tablets | White round tablets | White round tablets | White round tablets | White round tablets |
| Moisture (%) | <3.0 | 1.7 | 1.5 | 1.6 | 1.5 | 1.6 | 1.4 | 1.6 |
| Assay (%) | 95.0-105.0 | 100.0 | 100.1 | 100.7 | 99.9 | 100.0 | 100.1 | 100.4 |
| Hardness (Kp) | 3.0-6.0 | 4.4 | 4.7 | 3.2 | 3.4 | 3.5 | 3.0 | 4.3 |
| Friability (%) | <1.0 | 0.35 | 0.33 | 0.31 | 0.35 | 0.37 | 0.25 | 0.29 |
| Disintegration time (seconds) | <180 (<3 min) | 36 | 36 | 37 | 40 | 47 | 50 | 59 |
| Dispersion Quality | Passes through 710 um | in accordance | in accordance | in accordance | in accordance | in accordance | in accordance | in accordance |
| Dissolution (%) | ≧80.0 | 100.1 | 99.8 | 100.7 | 99.9 | 98.7 | 99.5 | 100.6 |
| Impurities (%) | Indiv: ≦0.5 | 0.4 | 0.4 | 0.3 | 0.3 | 0.2 | 0.3 | 0.4 |
|  | Total: ≦1.0 | 0.6 | 0.8 | 0.6 | 0.4 | 0.3 | 0.6 | 0.8 |

Discussion

Examples 1 to 4 refer to domperidone tables obtained by direct compression of all the components of the mixture and represent tablets which do not comply with the specifications in what concerns friability, disintegration times or both.

Examples 5-10 concern formulations comprising D-mannitol as an "auxiliary" granulate obtained by wet granulation and mixed with the remaining components. Examples 5 and 6 present two disintegrating agents, i.e. microcrystalline cellulose and carboxymethylcellulose calcium. For both examples, disintegration times are very rapid (i.e. <1 min), but friability is >1.0%, thus out of specification.

Examples 7 to 10 present the optimised formulations, comprising only one disintegrating agent, i.e. microcrystalline cellulose, the parameters of which comply with all the specifications, i.e. hardness (i.e. 3-6 Kp), friability (i.e. <1.0%) and disintegration time (i.e. <1 min).

For the optimised formulations we observed that hardness should be between 3 and 6 Kp to assure that friability and disintegration times do not exceed specified values.

The amounts of microcrystalline cellulose and Mannitol granules could vary between 10 to 30% (w/w) and 60 to 80% (w/w) of the total weight of the tablet respectively, without exceeding the values of friability and/or disintegration times specified.

The domperidone dissolution profiles obtained for Motilium® tablets and for the water-dispersible tablets of the present invention suggest that the latter produce a pharmacological effect more rapidly than the conventional tablets.

The stability tests performed showed that the optimised formulations of the present invention are stable in the Polyamide/aluminium/PVC-Aluminium blister packaging material chosen, for a period of time adapted to the period of validity established for pharmaceutical products. According to CPMP/QWP/122/02, a drug is considered as stable if it is within the defined/regulatory specifications when stored at 25° C./60% RH (2 years) and 40° C./75% RH (6 months), which has been observed for the formulations of the present invention.

To comply with the defined specifications, the fast water-dispersible domperidone tablet formulations of the present invention should present the following characteristics:

1) An amount of domperidone or its pharmaceutically acceptable salts generally used in therapeutics with pharmacological efficacy;
2) An amount of microcrystalline cellulose between 10 and 30% (w/w) in relation to the total weight of the tablet, to assure the disintegration of the tablet within the period of time defined;
3) An amount of mannitol granules between 60 and 80% (w/w) in relation to the total weight of the tablet, the mannitol granules being prepared with D-mannitol and maize starch gum, to assure the flowability and compressibility of the mixture and the fast dissolution of the formulation;
4) A sweetener and a flavouring agent, to mask the active ingredient and to improve the taste of the dispersion;
5) A lubricant, to guarantee the good performance of the compression process of the mixture.

To obtain the intended specifications, tablets should be prepared according to the procedure briefly described as follows:

1) Mannitol granules are prepared by high shear granulation of D-mannitol with maize starch gum. The wet granules are dried at 45° C.±5° C. in a fluid bed drier or in a static horizontal oven to <3% moisture measured by the Karl-Fischer method. After drying, the granules are then calibrated through a 1.0 mm opening mesh size sieve.
2) The remaining dry components are calibrated through convenient mesh size sieves.
3) A pre-mixture with a half part of microcrystalline cellulose and domperidone is made and blended, then calibrated through a 0.7 mm diameter mesh size sieve.
4) Addition of the mannitol granules to the previous pre-mixture and the other half part of microcrystalline cellulose and blending for 15 minutes.
5) Addition of the remaining ingredients (sweetener and flavour) and blending for 15 minutes.
6) Lubricant is then added and the final mixture homogenised for only 3 minutes.

The invention claimed is:

1. Fast water-dispersible tablets containing domperidone for oral administration in an amount with therapeutic efficacy, comprising domperidone or pharmaceutically acceptable salts thereof, characterised in that they contain about 60-80% (w/w) of an auxiliary granulate and about 10-30% (w/w) of a disintegrating agent, expressed in relation to the total weight of the tablets, a sweetener, a flavouring agent and a lubricant, the formulations of which have an enhanced structural integrity, having a friability lower than 1.0%, and are able to disperse in water within 3 minutes, to provide a dispersion that passes through a 710 μm diameter mesh size sieve, that presents a pleasant taste and the absence of perceptible granules in the mouth, characterized in that the auxiliary granulate is D-mannitol granules comprising 3% of maize starch and 97% of D-mannitol, and present less than 3.0% moisture, determined by the Karl-Fishcer method.

2. Fast water-dispersible tablets according to claim 1 characterised in that the disintegrating agent is microcrystalline cellulose.

3. Fast water-dispersible tablets according to claim 1 characterised in that the sweetener agent is an artificial sweetener.

4. Fast water-dispersible tablets according to claim 1 characterised in that the flavouring agent is selected from the group consisting of natural flavouring agents and nature-identical flavouring agents.

5. Fast water-dispersible tablets according to claim 1 characterised in that the lubricant is selected from the group of hydrophobic lubricants.

6. Fast water-dispersible tablets according to claim 1 characterised in that tablet hardness values are between 3 and 6 Kp.

7. Fast water-dispersible tablets according to claim 1 characterised in that the dispersion times are lower than 2 minutes.

8. Fast water-dispersible tablets according to claim 1, designed in such a way that the final products display and maintain the stability characteristics related to the amount of active ingredient, moisture, hardness, friability, disintegration time, dispersion quality, dissolution assay and impurities, the values of which assure stability for at least 3 years.

9. Process for the preparation of mannitol granules in the fast water-dispersible tablets according to claim 1 characterised by the granulation of D-mannitol with maize starch gum through high shear granulation, drying of the obtained granules at 45° C.±5° C. in a fluid bed drier or in a static horizontal oven and calibration of the granules through 1.0 mm diameter mesh size sieve.

10. Process for the preparation of the fast water-dispersible tablets according to claim 1, in which a pre-mixture of domperidone and a half part of microcrystalline cellulose is made and calibrated through a 0.7 mm diameter mesh size sieve and, afterwards, mannitol granules and the remaining microcrystalline cellulose are added and blended for 15 minutes, sweetening and flavouring agents are added and blended for 15 minutes and, at last, lubricant is added and the final mixture homogeneized for a short period of time.

11. Fast water-dispersible tablets according to claim 1 characterised in that the sweetener agent is sodium saccharin.

12. Fast water-dispersible tablets according to claim 1 characterised in that the flavouring agent is selected from artificial flavouring agents.

13. Fast water-dispersible tablets according to claim 1 characterised in that the lubricant is magnesium stearate.

14. Fast water-dispersible tablets according to claim 1 characterised in that the dispersion times are lower than 1 minute.

15. Fast water-dispersible tablets according to claim 2 characterised in that tablet hardness values are between 3 and 6 Kp.

16. Fast water-dispersible tablets according to claim 3 characterised in that tablet hardness values are between 3 and 6 Kp.

* * * * *